United States Patent [19]

Yeager et al.

[11] Patent Number: 4,483,748
[45] Date of Patent: Nov. 20, 1984

[54] AUTOMATED MEMBRANE TEST CELL APPARATUS AND METHOD FOR SO USING

[75] Inventors: Howard L. Yeager; J. David Malinsky, both of Calgary, Canada

[73] Assignee: Olin Corporation, New Haven, Conn.

[21] Appl. No.: 420,413

[22] Filed: Sep. 20, 1982

[51] Int. Cl.³ .................... G01N 27/28; G01N 27/40
[52] U.S. Cl. .................................. 204/1 T; 204/406; 204/409; 204/415; 204/435
[58] Field of Search .............. 204/1 T, 406, 409, 415, 204/435

[56] References Cited

U.S. PATENT DOCUMENTS

| | | | |
|---|---|---|---|
| 3,556,950 | 1/1971 | Dahms | 204/409 |
| 3,654,113 | 4/1972 | Bochinski | 204/406 |
| 3,672,843 | 6/1972 | Rosse et al. | 204/406 |
| 3,718,568 | 2/1973 | Neuwelt | 204/1 T |
| 4,189,367 | 2/1980 | Connery et al. | 204/1 T |
| 4,379,020 | 4/1983 | Yeager | 204/1 T |

OTHER PUBLICATIONS

Peter J. Smith and Trevor L. Jones, "The Development and Application of a Small Cell for the Determination of Ionic Transport Numbers by Use of Radiotracers", presented at the American Chemical Society, (Polymer Division), Workshop on Perfluorinated Ionomer Membranes, Feb. 1982 at Orlando, Florida.

Primary Examiner—R. L. Andrews
Assistant Examiner—Terryence Chapman
Attorney, Agent, or Firm—Arthur E. Oaks; Donald F. Clements; Thomas P. O'Day

[57] ABSTRACT

An automated electrolytic membrane test cell apparatus adaptable for the purpose of accurately measuring cationic transport and water transport numbers for membranes used in chlor-alkali cells under operating conditions similar to those used in such cells is disclosed. The apparatus comprises a test cell, said test cell being adapted to hold a permselective membrane sealingly supported therein so as to create separate anode and cathode compartments, each of said compartments having a suitable electrode, and heating electrolyte inlet and outlet means attached thereto. The apparatus further comprises means to select one of a plurality of anolyte and catholyte test solutions and control means adapted to control the electrolysis, circulation and heating of said solutions and the generation of all test samples needed to perform the measurements necessary to calculate said transport numbers. When used in conjunction with radioactive tracer techniques, considerably improvements are possible in the accuracy and ease with which transport phenomena in said membrane can be studied.

37 Claims, 9 Drawing Figures

AUTOMATED MEMBRANE TEST CELL APPARATUS AND METHOD FOR SO USING

BACKGROUND OF THE INVENTION

The present invention relates generally to membrane type electrolytic cells for the production of chlorine, alkali metal hydroxides and hydrogen and more particularly to an apparatus and method adapted for experimental studies of the cationic and water transport phenomena associated with said membrane.

Chlorine and caustic are essential, large volumn commodities used in all industrial societies. They are produced almost entirely electrolytically from aqueous solutions of alkali metal chlorides with the largest portion of such production coming from mercury and diaphragm cells. With the advent of technological advances such as dimensionally stable anodes, high activity catalytic cathodic materials and cation exchange, hydraulically impermeable permselective membranes, considerable improvements have been made in both product quality and energy efficiency. However, the complicated chemical structure of these membranes and their relative fragility make it difficult to optimize production parameters. For this, smaller cells are used to determine basic membrane characteristics, particularly their cationic and water transfer numbers and their dynamic properties under conditions typical of an operating cell.

Extensive literature exists on the determination of ionic and water transport numbers for ion exchange membranes. For cationic transport both Hittorf-type electrolysis experiments and indirect emf methods have been used. In similar fashion, membrane water transport numbers can be measured by electrolysis techniques or by streaming potential techniques. Aside from the systematic discrepancies which have been observed between emf and the true electrolysis results, the former techniques do not lend themselves to studies using a high current density.

Electrolysis methods based on measuring changes in either electrolytic solution volume or weight are known. Volume methods are generally more convenient, but are susceptible to error due to membrane movement and are difficult to use at elevated temperatures. With this approach, the best reported measurements of potassium ion transport numbers, at room temperature and low current density, have an average relative standard deviation of about 6%.

The need to create a measurable concentration change during electrolysis with this approach presents a further problem for cationic transport number measurements in concentrated solution environments. If concentration changes are kept small, it is difficult to obtain sufficient accuracy in solution analysis to obtain a reliable result. If larger concentration changes are produced, such membrane properties as water and electrolyte content are altered with the result that interpretation of the results becomes considerably more difficult.

It has been shown that the use of radioactive tracer techniques can be effective in removing the problem of concentration changes in the measurement of membrane transport parameters. These techniques have led to a considerable improvement in the accuracy with which measurement of membrane characteristics under conditions typical of those used in production cells can be made. A description of prior art methods and an improved test cell for performing such measurements by this technique are described in U.S. Pat. No. 4,379,029 issued to Howard L. Yeager, on Apr. 5, 1983 and assigned to Olin Corporation. However, even with this cell, it is still necessary to perform all operations manually, which both limits the complexity of the experimental procedures which can be used and greatly increases the time (about one full day) required to perform a measurement on any given membrane with any given set of test conditions. Part of this problem has been solved in a system described by Peter J. Smith and Trevor L. Jones in "The Development and Application of a Small Cell for the Determination of Ionic Transport Numbers by Use of Radiotracers" presented at the American Chemical Society (Polymer Division) Workshop on Perfluorinated Ionomer Membranes held in February, 1982 at Orlando, Fla. However, the semiautomatic test apparatus described therein is unable to programmably vary experimental parameters such as the brine or caustic concentrations or current density so that many of the limitations described with the fully manual systems are still present.

SUMMARY OF THE INVENTION

The automated apparatus and method of the present invention provides fully automatic means for measuring electrolytic membrane operating parameters such as cation and water transport numbers (mol/Faraday) under operating conditions similar to those used in many commercial chlor-alkali membrane cells. To do this, measurements can be made at temperatures up to about 100° C. and with a plurality of anolyte and catholyte solutions and current density ranges. In a preferred embodiment, the apparatus is adapted to utilize chloride brines up to full saturation, caustic solution concentrations up to about 16M and current densities between about 0.5 and about 15 KA/m$^2$.

A preferred embodiment of the apparatus of this invention comprises a test cell having a permselective membrane sealingly suspended therein so as to form separate anode and cathode compartments. Each of said compartments contain a suitable electrode and have attached fluid systems comprising a plurality of electrolyte storage cells for holding anolyte brines and catholyte liquors of different concentrations, and means for introducing, heating and circulating selected individual anolyte and catholyte solutions therethrough. The introduction and circulation of these solutions along with all other aspects of cell operation such as operating time, cell operating voltage and amperage is handled by associated programmable control means which are further adapted to generate test samples, command all necessary measurements, log the test data and calculate and display the transport numbers for a particular membrane at each set of solution concentrations. In one embodiment, the apparatus is adapted to use three anolyte brines, four caustic catholyte solution concentrations and at least two discrete cell amperage values. In use, these are controllably selected so as to produce a set of 24 Na$^+$ and H$_2$O transport numbers in considerably less time and with equal or superior accuracy as compared to prior art techniques.

Thus, the principal object of the subject invention is to provide an improved membrane test cell apparatus to automatically provide data on cation and water transport for permselective membranes of the types used in commercial chlor-alkali cells more quickly and accurately than heretofore possible.

It is a further object of the subject invention to provide a fully automatic membrane test cell apparatus which is readily adaptable to testing a wide variety of membrane materials under a full range of conditions such as are found in commercial membrane chlor-alkali cells.

Those and other objects and further scope of applicability of the present invention will become apparent from a reading of the detailed description to follow, taken in conjunction with the accompanying drawings.

DETAILED DESCRIPTION OF THE INVENTION

The apparatus and method of the present invention are adapted to provide, among other things, data as to the cationic transport phenomena observed in advanced membranes used in the chlor-alkali industry. The following discussion is wholly in terms of sodium ion transport in a chloride brine. However, it is obvious that it could just as easily be used for other alkali and alkaline earth metal ions either alone or in combination or with solutions containing other anions. Such use is considered to be fully within the ambit of this disclosure.

Figures 1, 5:
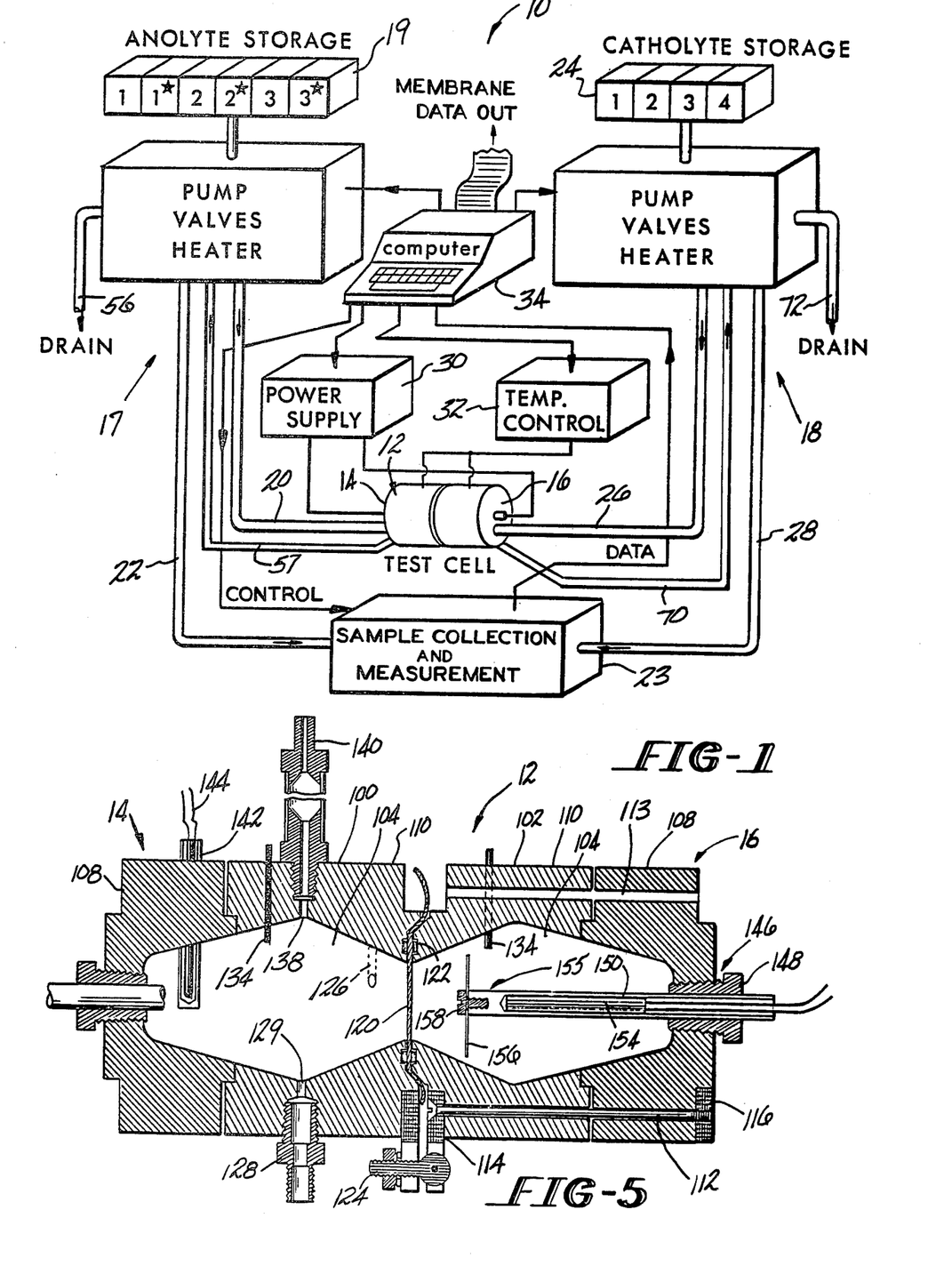
FIG. 1 is a schematic drawing showing the apparatus of the present invention.
FIG. 5 is a cross sectional view of the cell of FIG. 4 along the line 5—5.

Referring now to FIG. 1, a schematic drawing of the automated membrane test cell apparatus 10 of the present invention is shown. Apparatus 10 comprises a test cell 12 having an anode compartment 14 and a cathode compartment 16 therein and further having associated with it anolyte fluid system 17 and catholyte fluid system 18. Anolyte fluid system 17 further comprises multicompartmented anolyte storage containers 19 and associated inlet supply lines 20 and 22 leading to anode compartment 14 and sample collection and measurement subsystem 23, respectively. Catholyte fluid system 18 similarly comprises multicompartmented catholyte storage containers 24 and inlet supply lines 26 and 28 to cathode compartment 16 and sample collection and measurement subsystem 23, respectively.

Also associated with the apparatus are power supply 30 and temperature controller 32, the function of which will be described hereinbelow. Acting in a supervisory capacity is central control system 34. This controls fluid flows, causes the necessary generation of test samples, retrieves and logs the measurement data from which it calculates and displays the membrane transport numbers of interest.

Figure 2:
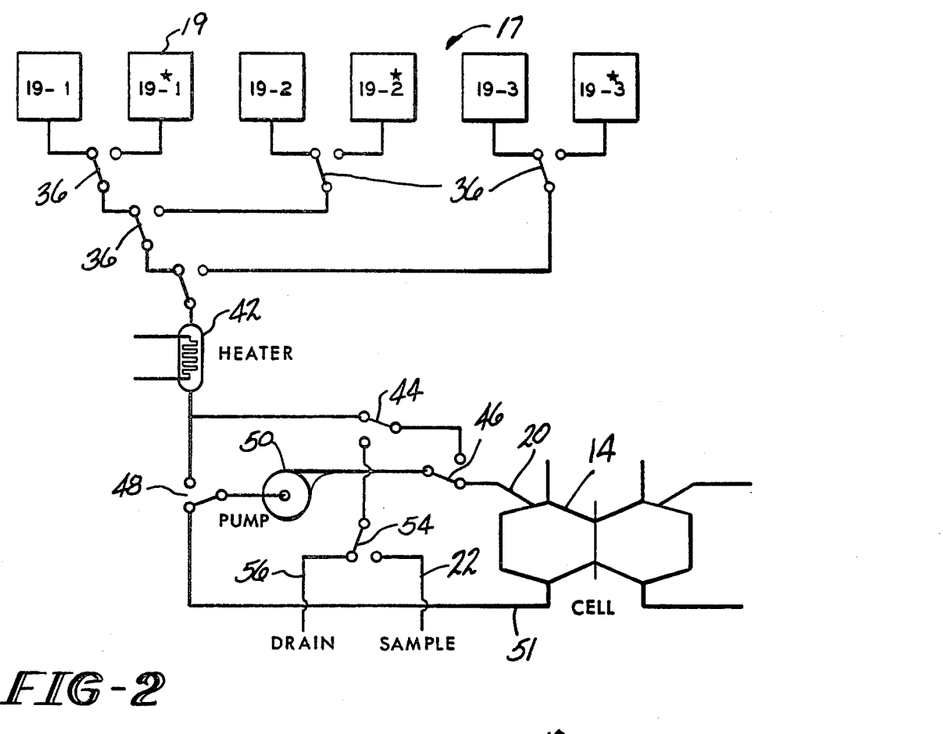
FIG. 2 is a schematic drawing of the brine in the subsystem used with the test cell of FIG. 1.

Referring to FIG. 2, anolyte storage containers 19 is shown to be comprised of a plurality of paired storage containers 19-1, 19-1*, 19-2, 19-2*, etc., preferably made of polyethylene, and adapted to hold the anolyte brine solutions used to measure membrane $Na^+$ and $H_2O$ transport properties. The containers with starred numbers hold brine solutions having the same overall concentrations as those in their companion but with between about 30 and about 60 microcuries of radioactive tracer Na-22 added thereto. As shown, there are three pairs of containers, each having a separate outlet opened by one of a plurality of bipolar selector valves 36. These are configured to admit, upon command from central control system 34, the contents of a selected storage container 19 into anode compartment 14 through preheating means 42, wherein said solution is heated. The heated solution can be fed into inlet line 20 and anode compartment 14 either directly through bipolar selector valves 44 and 46, or through bipolar selector valve 48 and pump 50. Once anode compartment 14 is filled, the valves 46 and 48 are configured by central control system 34 so that the anolyte brine is circulated through recycle line 51 and inlet line 20 by pump 50.

At the completion of a particular portion of the test measurement procedure, anode compartment 14 is emptied by central control system 34 resetting valves 44 and 46 to now direct the flow from pump 50 into bipolar selector valve 54. This, in turn, directs the output flow either into drain line 56 or through supply line 22 to sample collection and measurement subsystem 23 as required.

Figure 3:
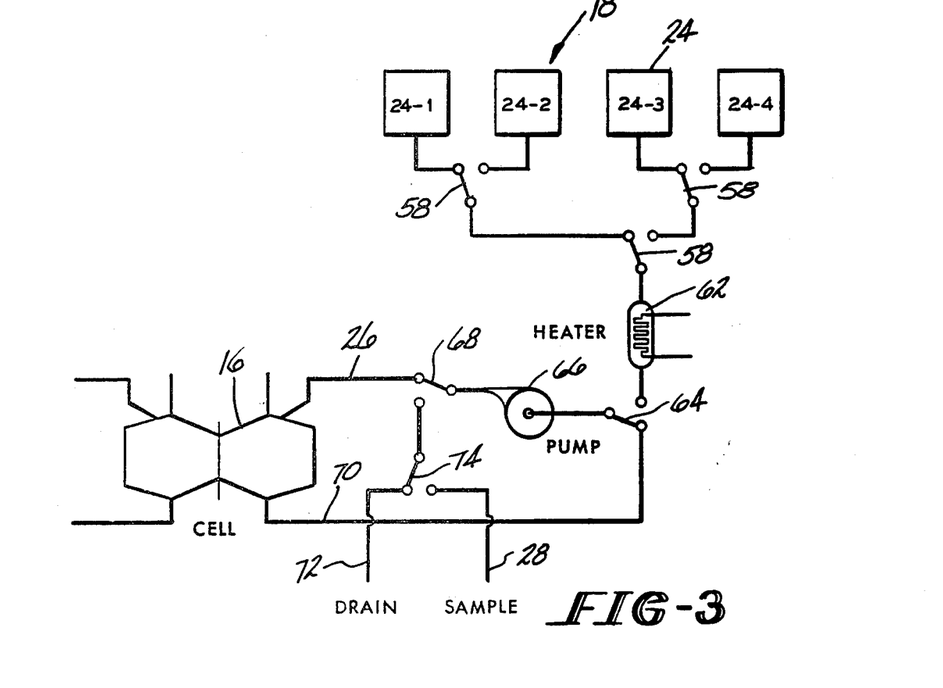
FIG. 3 is a schematic drawing of the caustic subsystem used with the test cell of FIG. 1.

As shown in FIG. 3, catholyte fluid system 18 is similarly configured. Thus, it has a plurality of catholyte storage containers 24, comprised of four individual polyethylene catholyte storage containers 24-1, 24-2, etc. adapted to hold catholyte caustic liquors of differing concentrations as used in the test procedures described below. These storage containers are arranged in pairs, each of which is connected through one of a plurality of a bipolar selector valves 58 to heating means 62, bipolar selector valve 64, pump 66 and bipolar selector valve 68 and inlet line 26 leading to cathode compartment 16. Circulatory flow is achieved within catholyte fluid system 18 and cathode compartment 16 in substantially the same manner as with anolyte fluid system 17 with valves 64 and 68 being configured by central control system 34 to direct the flow from pump 66 through inlet line 26 into cathode compartment 16 and back to pump 66 through recycle line 70. Similarly, at the completion of a test cycle, valve 68 is reset to now feed the discharge from recycle line 70 through bipolar selector valve 74 either into drain line 72 or through supply line 28 and sample collection and measurement subsystem 23.

To provide service with minimum attention, pumps 50 and 66 must be able to self-prime and be constructed of materials which will withstand the corrosive anolyte and catholyte solutions. One such pump is a model 902-1722-2 pump manufactured by the Mace Corporation of South El Monte, Calif. and which is constructed of polytetrafluoroethylene. Further, it has been found that even with such a pump, suitable functioning of the system can only be obtained by the use of substantially leak-proof check valves on the inlet and outlet ports of the two pumps.

Figure 4:
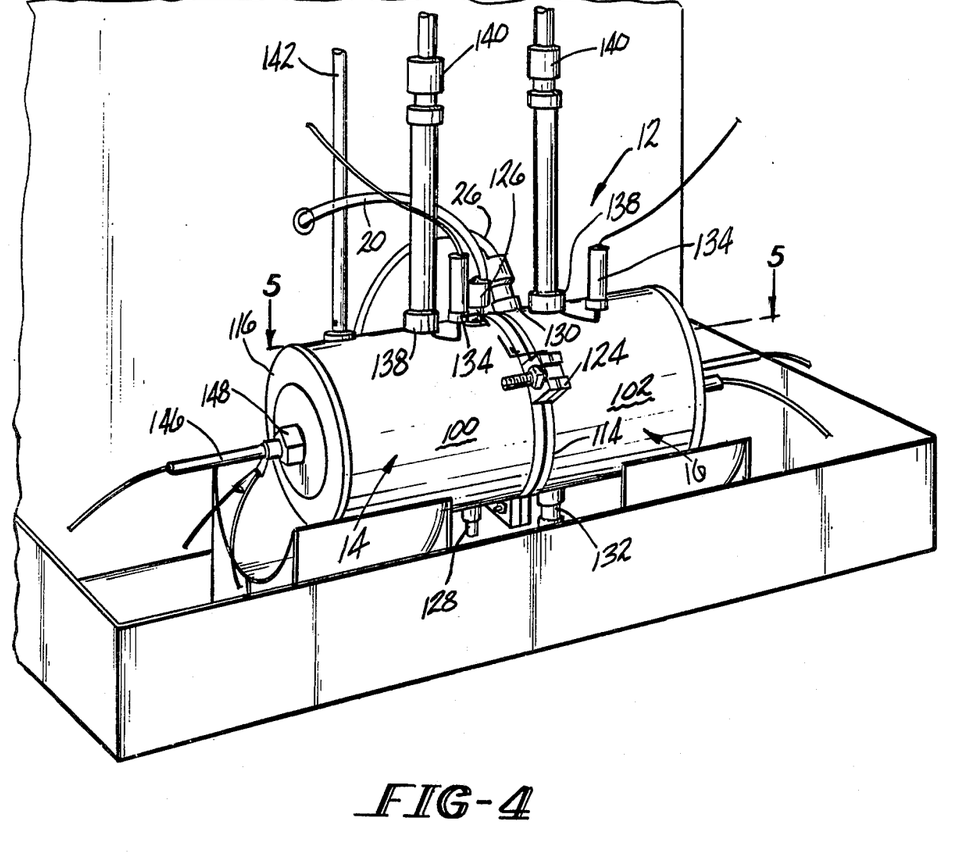
FIG. 4 is an isometric view of a test cell as used in the apparatus of the present invention.

Overall isometric and sectional side views of test cell 12 are shown in FIGS. 4 and 5. As shown in FIG. 5 and partially in FIG. 4, the cell comprises anode and cathode half cells 100 and 102, each containing a horizontally disposed chamber 104, opened at one end, said cell being formed when said half cells are aligned and abut each other at the opened ends. Each half cell is further divided into two quarter cell sections 108 and 110 to facilitate construction and installation of inlet and outlet ports and electrodes. Each pair of quarter cells is designed so as to provide a smooth interior surface and a fluid-tight seal. Although chamber 104 could be cylindrical or conical in shape, the truncated biconic shape illustrated is preferred. Such a configuration is particularly well adapted to ensure good current density distribution at the membrane, optimum drainage for solution recovery, and good gas bubble disengagement above the solution level. Quarter cell sections 108 and 110 are held together by a plurality of bolts 112 (only one being shown) which extend through bolt holes 113. Bolts 112 engage inner flange 114 and an outer flange 116 to hold the sections tightly together to form half cells 100 and 102. All major structural components of half cells 100 and 102 are made of an inert material such as polytetrafluoroethylene. This allows the system to operate in a temperature range of between about 60° and 200° C., with about 80°–100° C. being preferred. Further, it can tolerate fully saturated brine solution concentrations, with about 2–4M being preferred and caustic liquor concentrations between about 3 and about 16 molar, with about 8 to about 15M being preferred. A current density of between about 0.5 and about 15 KA/m$^2$ can be used, with about 1 to about 10 KA/m$^2$ being preferred.

Sealingly suspended between chambers 104 is permselective membrane 120 which separates said chambers to form anode compartment 14 and cathode compartment 16 of a complete membrane cell 12. In general, these are perfluorinated polymers having lateral side chains, said chains selected from the group consisting of sulfonic, carboxylic and phosphonic acid functional groups, with or without amine modification and/or fabric reinforcement. Membranes of this type are described in U.S. Pat. Nos. 4,065,366 issued to Oda et al and 4,036,714 issued to Spitzer, both being incorporated herein by reference. Leak integrity of the cell is provided by sealing gasket 122 and a plurality of lock bolts 124 which engage and clamp the two inner flanges 114 tightly together.

As shown in FIG. 4 and partially in FIG. 5, drilled into each half cell assembly are a plurality of ports which are used for filling and draining of electrolytes, venting of gases and the introduction of electrodes, heaters and monitors for cell temperature as required. Anolyte brine enters half cell 100 through inlet line 20 and inlet port 126 and is discharged through outlet port 128 which is set at its lowermost point. Catholyte caustic liquor is admitted through inlet line 26 and inlet port 130 and discharged through outlet port 132. In both cases, the proper fill height is sensed by a secondary electrode 134, preferably made of platinum, inserted into the top of each half cell, using an AC conductive circuit in conjunction with central control system 34. When each chamber is filled, the particular storage chamber feeding the half cells is closed and the fluid circulation system activated. Gases (hydrogen, chlorine and water vapor) generated during electrolysis are discharged through gas discharge ports 138, having a drying tube 140 attached thereto. Where water transport numbers are determined, tube 140 must be weighed before and after each run to determine the amount of water evaporated during the electrolysis. Means for doing this, such as load cells, are well known in the industry. Temperature monitor tube 142 which holds temperature monitor 144 of FIG. 5 is inserted into half cell 100.

Figure 6:
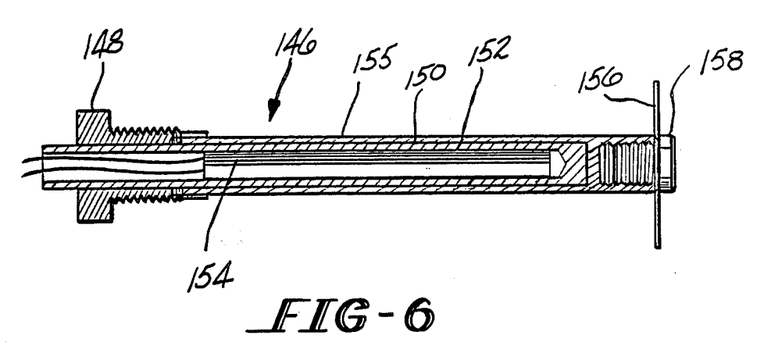
FIG. 6 is a cross sectional view of a combined electrode and heater as used in the anode and cathode compartments of the cell of FIG. 5.

Inserted through and mounted onto each end of cell 12 is a primary electrode assembly 146. As shown in FIG. 6, this comprises a hollow mounting nut 148 which threadingly engages the outermost end wall of the cell to sealingly hold hollow electrode shaft 150 tightly within anode compartment 14 and cathode compartment 16. Within the hollow portion 152 of each of these shafts is heating means 154, preferably a cartridge heater, which sets up and maintains, in conjunction with temperature controller 32, central control system 34, and the two cell fluid circulating systems, the temperature at which any particular test determination will be made. An electrode 155 is mounted at the innermost end of shaft 150. In both compartments, in the preferred embodiment, this comprises a foraminous disc 156 which is held in place by mounting screw 158. On the anode side, the shaft and screw are preferably made of titanium with the electrode disc being made of a ruthenium oxide/titanium oxide coated titanium screen. On the cathode side, the shaft and screw are preferably made of Nickel 200 alloy and the electrode disc of platinum. In both cases, the electrode disc 156 is about 4 centimeters in diameter. This arrangement allows the changing and quick positioning of the electrode assembly 146 within the cell so that a variety of experimental conditions can be evaluated at low cost, thus, increasing the overall versatility of the system. Similarly, the design of electrode 155 allows the quick evaluation of a wide variety of advanced electrode materials such as dimensionally stable anodes and catalytic cathodes such as the Beta phase Raney nickel - molybdenum materials described by Gray in U.S. Pat. No. 4,240,895. Further, the system design shown is readily adaptable to allow additional electrodes to be inserted to monitor the dynamic voltage drop across the membrane so that its characteristics as a function of cell power level can be determined. Such modifications are considered to be within the ambit of this invention.

TEST PROCEDURE

The transport numbers of interest are measured by a procedure which comprises "pre-electrolyzing" portions of brine and caustic solutions having preset concentrations of NaCl and NaOH, at a preset temperature and cell amperage. After a suitable time to achieve thermal and electrical equilibrium, samples are removed and titrated for hydroxyl and chloride ion. The anolyte solution is then replaced with one containing the same overall chloride ion concentration but containing about 30 to about 60 microcuries of Na-22 tracer and electrolysis continued. After a suitable period of time, the anolyte and catholyte solutions are removed, weighed and counted for Na-22 tracer activity. The methods, by which the transport numbers are computed, are as follows:

1. Sodium ion transport number.

The moles of sodium ion which are transported through the membrane during electrolysis are calculated from the original specific activity of the anolyte solution ($A_a$, counts/minute/gram solution), the specific activity of the catholyte solution, $A_c$, the original concentration of the anolyte solution, $C_a$, and the final weight of the catholyte solution, $W_{cf}$.

$$\text{mol}_{Na+} = \frac{C_a}{A_a}(A_c W_{cf})$$

The sodium ion transport number is then calculated from the equation:

$$t_{Na+} = \frac{(\text{mol}_{Na+})(96,487)}{[i(\text{amp})][t(\text{seconds})]} \quad (1)$$

2. Water transport number.

First the moles of salt in the final catholyte solution are calculated from the weight and concentration of that solution. Then the weight of water is calculated. Finally, the weight of water in the original catholyte solution is calculated in similar fashion and the difference, $\Delta w$, is determined. The transport number of water is calculated from the equation:

$$t_{H_2O} = \frac{(\Delta w)(96,487)}{(18.01)[i(\text{amp})][t(\text{seconds})]} + 1 \quad (2)$$

The apparatus of the present invention is adapted to accomplish these results by automatically cycling the cell through three different brine concentrations, four different caustic concentrations and two different cell amperages. Further, it is adapted to generate all necessary test samples, weigh and count them, log the data and when all necessary data are collected, calculate the transport numbers of interest.

For each given pair of selected brine and caustic solutions, the sequence of operation for each measurement comprises six separate steps as follows:
 1. Membrane conditioning and equilibration.
 2. Low amperage pre-electrolysis.
 3. Low amperage electrolysis.
 4. Membrane re-equilibration.
 5. High amperage pre-electrolysis.
 6. High amperage electrolysis.

For a complete membrane $t_{Na+}$ analysis, steps 1 to 6 are repeated by changing solution concentrations in the following order:

| Test | Brine Solution | Caustic Solution |
|------|----------------|------------------|
| 1    | 1              | 1                |
| 2    | 2              | 1                |
| 3    | 3              | 1                |
| 4    | 1              | 2                |
| 5    | 2              | 2                |
| 6    | 3              | 2                |
| 7    | 1              | 3                |
| 8    | 2              | 3                |
| 9    | 3              | 3                |
| 10   | 1              | 4                |
| 11   | 2              | 4                |
| 12   | 3              | 4                |

In normal operation, the solution concentrations increase as they are changed so that brine/caustic combination 1-1 is the most dilute and combination 3-4 the most concentrated. Once the unit is set into operation, it will cycle through all 12 of these tests with only minimal supervision.

The details of each experimental measurement are as follows:

MEMBRANE CONDITIONING AND EQUILIBRATION

As a necessary part of each experimental sequence, membrane 120 must first be conditioned before it can be used. This is done, generally, by soaking it at a temperature between about 80° and about 90° C. in between about 4 and about 6 molar NaOH solution for about 8 to about 10 hours, before first mounting between the two halves of test cell 12.

Once the cell is fully assembled, the membrane is then equilibrated with valves 36, 48 and 46 being set to allow a selected brine solution to flow from one of anolyte storage containers 19 through anolyte preheating means 42 into anode compartment 14. Although the system can be configured to allow gravity feed, the use of pump 50 is preferred to promote smooth controlled flow into anode compartment 14. Preheating means 42 is activated during the filling operation to heat the solution to a preselected operating temperature. Once this is reached, it is then thermostatically controlled by temperature controller 32 to about ±1° C. to avoid overheating the solution. During the fill cycle, pump 50 is cycled on for about 0.5 second and off for about 1.0 second. Filling of the compartment is completed when the solution makes contact with level testing electrode 134 after which the system is configured to allow circulation of the solution. A similar operation is used to admit a selected catholyte caustic solution to cathode compartment 16.

After both sides of test cell 12 are filled, the pumps and heaters are turned off, an electronic timer (not shown) in central control system 34 is started and cartridge heater 154 is turned on to maintain the solutions at the preset temperature. Each minute, the pumps are turned on and the solutions circulated for between about 3 and about 6 seconds to keep the system in thermal equilibrium. This procedure is continued for between about 1¾ and about 2½ hours, if the most recent solution change has been in NaCl concentration (for example, between tests 1 and 2). However, if the caustic solution concentration has also incremented (as after test 3) or if an experimental sequence has been started, a longer equilibration time of about 5 to about 7 hours must be used.

At the conclusion of these times, the solutions are discarded and anode compartment 14 and cathode compartment 16 are refilled with fresh solutions of the same concentrations and the above procedures repeated. In the 12-test cycle described above, the brine concentration is incremented twice before the caustic concentration is changed so that a total of about 40 hours of equilibration time is required. The automatic timing and filling features of the present invention assures that membrane equilibration will be properly conducted with only minimum human supervision.

LOW AMPERAGE PRE-ELECTROLYSIS

At the end of the equilibration time, the anode and cathode compartments are drained and refilled with solutions of the desired concentrations, starting with storage containers 19-1 and 24-1 as described hereinabove. The pumps and internal cartridge heater 154 are turned on and recirculation and heating continued, for example, for about 8 minutes until the system comes to a preset equilibrium temperature. At the end of this time, electrolysis is begun with central control system 34 activating power supply 30 to provide a preset, "low" current density, most usually about 2 KA/m² (or 1.2 amperes for a membrane area of about 6.00 cm²) with heating and pumping continuing uninterrupted. Electrolysis under these conditions is continued for about 8 to about 12 minutes to further condition the membrane to its environment. At the conclusion of this time, the cartridge heaters and electrolysis current are shut off and a "pretest" or blank sample of the catholyte solution is taken in a pre-weighed vial with the remainder of the solutions being pumped to the drains and discarded.

LOW AMPERAGE ELECTROLYSIS

The above procedure for filling and recirculating the brine is repeated except that valves 36 are now set to introduce a brine solution from storage containers 19-1*. As noted, this has the same salt concentration as that in storage containers 19-1 but contains approximately 30 to 60 microcuries of Na-22 tracer. The electrolysis procedure described above is repeated for about 10 minutes after which the fluid flow system is reconfigured so as to feed the brine and caustic solutions into sample collection and measurement subsystem 23. In this, a 5 to 10 milliliter sample of radioactive brine and the entire catholyte solution is collected in pre-weighed containers. These containers are capped with pre-weighed caps, weighed, counted to measure the changes in radioactivity levels and the data logged in by central control system 34. For the containers and caps, any inert material may be utilized with polyethylene and polytetrafluoroethylene being preferred.

MEMBRANE RE-EQUILIBRATION

Any residual radioactivity remaining in the membrane is removed by reintroducing tracer-free brine and caustic into the anode and cathode compartments and recirculating them as described above for initial membrane equilibrium except that the treatment time is reduced to about 1 hour.

HIGH AMPERAGE PRE-ELECTROLYSIS

Fresh brine and caustic solutions are admitted into the cell and the pre-electrolysis procedure described above is repeated for about 2–3 minutes at the "higher" amperage which will be used in the phase of the experiment. In the studies described herein, this value was preset to be about 4 KA/m² or 2.4 A but other values could be used.

HIGH AMPERAGE ELECTROLYSIS

The electrolysis and sampling procedures described above for low amperage electrolysis are repeated except that the electrolysis time is reduced to about 5 minutes.

At the conclusion of this run, the system is configured to change the brine concentration, i.e. to introduce solutions from storage containers 19-2 and 19-2* with the procedures for membrane equilibration and electrolysis being repeated.

The running time for steps 2 to 6 in each of these tests in about 2 hours and with the equilibration times included, the full cycle from solutions 1—1 to 3-4 takes about 3 days to complete, the whole system being controlled automatically during this time. With prior art manual systems, such an experimental procedure would take at best a minimum of 10–12 days to complete.

The application of the apparatus of the present invention is illustrated by the following examples:

EXAMPLE 1

Cell 12 was assembled with a Nafion ® 901 hours in 5 M NaOH at a temperature of 85° C. For the experiment described herein, the cell held about 150 cc of solution in each compartment and the membrane active area was about 6 cm². This membrane is a carboxylic-sulfonic composite membrane with fabric reinforcement, manufactured by DuPont. Storage containers 19 and 24 were charged with a set of 3 M, 4 M and 5 M NaCl and 9.5 M, 11 M, 12.5 M and 13.5 M NaOH solutions respectively. Using the procedure described above, a set of 12 experimental runs at 84° C. was conducted to provide a total of 24 values for Na+ ion transport numbers, 12 at a current density of 2 KA/m² and an additional 12 at a current density of 4 KA/m². At the proper point in each sequence of operation, central control system 34 was programmed to generate, weigh and count the samples in collection and measurement subsystem 23 to determine the values of $A_a$, $A_c$ and $W_{cf}$. These along with previously inserted values for the molar concentrations of salt and caustic are used to calculate the values of $t_{Na+}$ and $t_{H_2O}$ as defined by equations (1) and (2) above. Each set of experimental values was logged in by central control system 34 and after the full experimental sequence was completed, a set of transport numbers was computed and presented. A typical set of these values are presented as Table I.

TABLE I

Sodium ion transport number for Nafion ® 901 membrane at two membrane current densities, 84° C.

| Concentration NaOH | 2 KA/m² Concentration NaCl | | | 4 KA/m² Concentration NaCl | | |
|---|---|---|---|---|---|---|
| | 3.0 M | 4.0 M | 5.0 M | 3.0 M | 4.0 M | 5.0 M |
| 9.5 M | — | 0.918 | 0.905 | 0.840 | 0.908 | 0.905 |
| 11.0 M | 0.906 | 0.940 | 0.965 | 0.928 | 0.945 | 0.948 |
| 12.5 M | 0.938 | 0.944 | 0.961 | 0.952 | 0.961 | 0.952 |
| 13.5 M | 0.938 | 0.950 | 0.935 | 0.953 | 0.964 | 0.920 |

Figure 7:
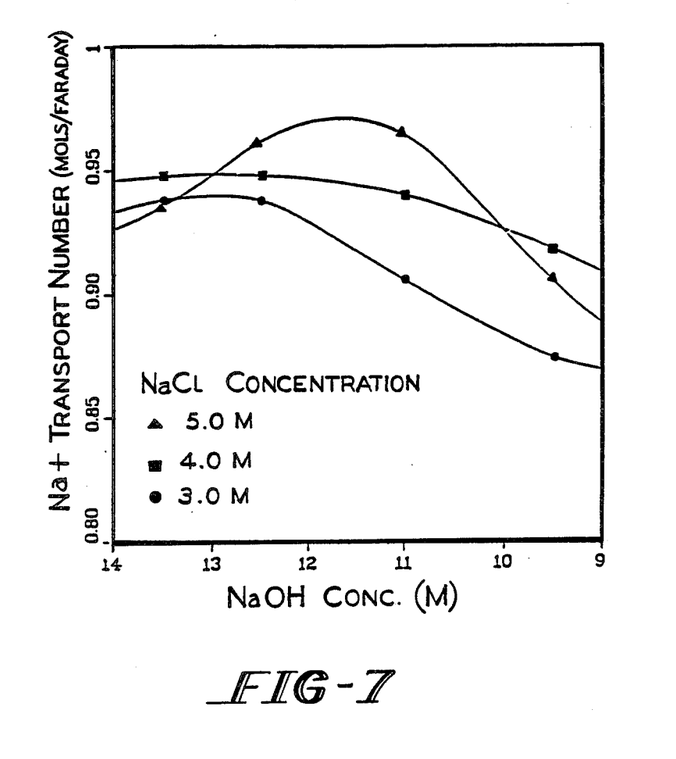
FIG. 7 is a plot of the sodium ion transport data at 84° C. and 2 $KA/m^2$ as obtained from the apparatus of the present invention.

In order to reveal trends in these data, a graphical presentation format was also used. This is based on cubic spline curve fitting technique disclosed by A. K. Cline in *Comm. of Assoc. Computer Machinery*, 17, pages 218–220 (1974) which produces a set of points showing the dependence of sodium transport numbers as a result of changes in sodium hydroxide concentration for each of the three sodium chloride brine concentrations used. Trend curves are generated by using the same technique to interpolate the intermediate points for the three original spline functions. A typical set of these curves for 2 KA/m² experiments at 84° C. is shown as FIG. 7.

Figure 8:
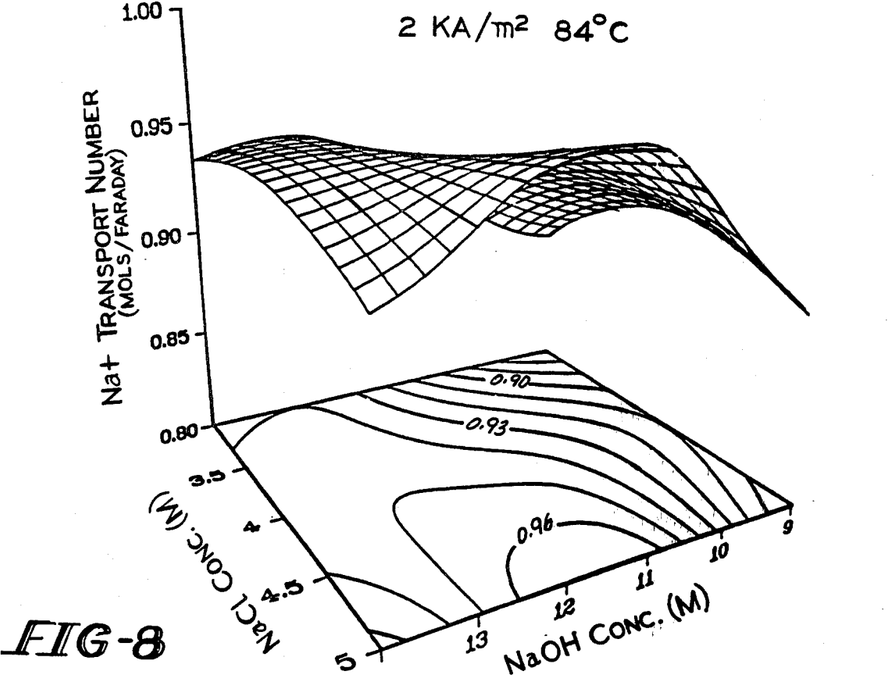
FIG. 8 is a computed three-dimensional plot of a membrane performance surface for a Nafion®901 membrane at 2 $KA/m^2$ and 84° C. as provided by the apparatus of the present invention.

These data are also used to generate membrane "performance" surfaces which show the inter-relationshps of brine and caustic concentrations on $t_{Na+}$. Such a surface for a 2 KA/m² experiment at 84° C. is shown as FIG. 8. To aid in the interpretation of these data, topographic projections of the surface are made onto the concentration plane. The standard deviation for these data is estimated to be less than 0.005 mol/F.

EXAMPLE 2

The experimental and computational techniques of Example 1 were repeated but at a cell equilibrium temperature of 90° C. The computed test results at 2

Figure 9:
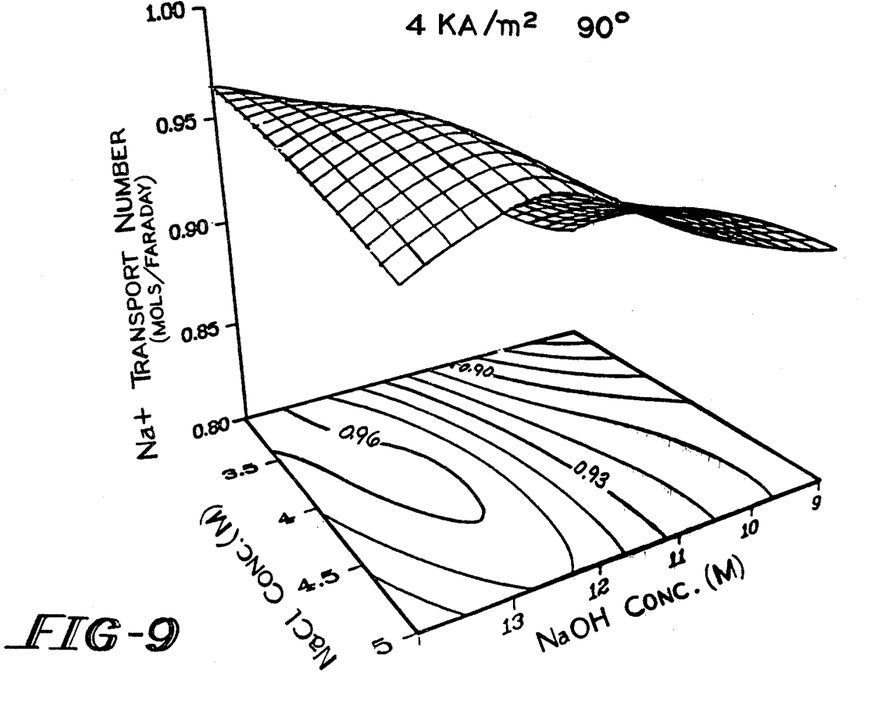
FIG. 9 is a computed three-dimensional plot of a membrane performance surface for a Nafion®901 membrane at 4 $KA/m^2$ and 90° C. as provided by the apparatus of the present invention.

KA/m² and 4 KA/m² are given in Table II and a 4 KA/m² performance surface is shown as FIG. 9.

TABLE II

Sodium ion transport number for Nafion ® 901 membrane at two membrane current densities, 90° C.

| Concentration NaOH | 2 KA/m² Concentration NaCl | | | 4 KA/m² Concentration NaCl | | |
|---|---|---|---|---|---|---|
| | 3.0 M | 4.0 M | 5.0 M | 3.0 M | 4.0 M | 5.0 M |
| 9.5 M | 0.862 | 0.886 | 0.914 | 0.866 | 0.902 | 0.908 |
| 11.0 M | 0.875 | 0.928 | 0.931 | 0.898 | 0.922 | 0.927 |
| 12.5 M | 0.919 | 0.966 | 0.936 | 0.941 | 0.961 | 0.951 |
| 13.5 M | 0.939 | 0.969 | 0.946 | 0.960 | 0.959 | 0.940 |

TEST INTERPRETATION

The current efficiency as reflected by the cationic transport numbers for the Nafion ® 901 membrane is reported by the manufacturer to reach 95% or higher over a caustic concentration range of 10 to 12.5M and to be greater than 90% over the entire concentration range. The data generated by the apparatus of this invention as shown in Examples 1 and 2 relatively quickly and easily demonstrate general agreement with this claim. Further, they show that the maximum $t_{Na+}$ values for this membrane shift to lower concentrations as cell operating temperatures and current density increase. Such data are important factors in not only evaluating membrane capabilities but in setting cell operating parameters to optimize performance.

This invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and range of equivalency of the claims are therefore intended to be embraced therein.

We claim:

1. A method of measuring cationic and water transport numbers for a selected cation exchange permselective membrane in a test system, said system comprising a test cell, said cell having said membrane sealingly suspended therein to form separate anode and cathode compartments for containing anolyte and catholyte solutions, respectively, and central control means for sequentially controlling the circulation and the temperature of said solutions, generating samples and performing test measurements on said samples to calculate said transport numbers, said method comprising:
(a) preparing a series of anolyte pairs, each member of said pair having the same anolyte concentration, each anolyte pair having a different anolyte concentration from other pairs in said series, one member of each pair containing a preselected amount of radioactive tracer material;
(b) preparing a series of catholytes, each catholyte having a different preselected catholyte concentration from other members of the series;
(c) under the automatic control of said central control means,
(1) conveying a portion of a first anolyte member of a selected anolyte pair to said anode compartment and a portion of a selected first catholyte from said series of catholytes to said cathode compartment, and circulating said first anolyte member and said first catholyte in said cell at a preselected temperature to condition said membrane;
(2) removing said anolyte and catholyte solutions and replacing them with fresh portions of the same anolyte and catholyte solutions used in step c (1);
(3) circulating said fresh portions, heating them to a preselected temperature, while electrolyzing them at a first preselected cell operating amperage for a preprogrammed period of time and at the conclusion of said time, separating a sample of said catholyte solution;
(4) removing said first anolyte member from said anode chamber and conveying to said anode chamber a portion of a second anolyte member from said pair containing radioactive tracer material;
(5) repeating said heating and circulating stage at said first cell preselected operating amperage to electrolyze said anolyte and catholyte solutions for a preselected period of time, said electrolysis producing a transfer of said tracer material from said anode compartment through said membrane into said cathode compartment and at the conclusion of said time, removing said solutions, separating samples, determining the change in the radioactive levels of said tracer in said anolyte and catholyte solution and logging said data;
(6) replacing said solutions with a second portion of the solutions used in step c(1) and circulating and heating said solutions for a second preset period of time to cleanse said membrane of said radioactive tracer;
(7) repeating steps c(2) to c(5) but at a second preselected cell operating amperage;
(8) measuring the net change of water content of the electrolyte in each compartment, said quantities being utilized in calculating the moles of water which have been transferred; and
(9) repeating steps c(1) to c(8) until said membrane is tested for each of said pair of anolytes in said series against each anolyte in said series, and calculating water transport numbers and cationic transport numbers for the membrane for each combination of said selected anolytes and said selected catholytes for said first and second preselected current density levels whereby a full set of transport numbers describing the response of said membrane is determined.

2. The method of claim 1 wherein said electrolyzing is performed at a current density of between about 0.5 and about 15 KA/m².

3. The method of claim 2 wherein said electrolyzing is performed at a current density of between about 1 and about 10 KA/m².

4. The method of claim 1 wherein said electrolytic solutions are heated to a temperature of between about 60° and about 200° C.

5. The method of claim 4 wherein said solution temperature is between about 80° and about 100° C.

6. The method of claim 1 wherein said anolyte solution is a chloride brine and said catholyte solution is a caustic liquor.

7. The method of claim 6 wherein the concentration of said chloride brine is between about 1 and about 5 molar.

8. The method of claim 7 wherein said chloride concentration is between about 2 and about 4 molar.

9. The method of claim 6 wherein the concentration of said caustic liquor is between about 3 and about 16 molar.

10. The method of claim 9 wherein the concentration of said caustic liquor is between about 8 and about 15 molar.

11. The method of claim 6 wherein said brine is comprised of a sodium chloride solution and said caustic liquor is comprised of a sodium hydroxide solution.

12. The method of claim 1 wherein said tracer element is Na-22.

13. The method of claim 1 further comprising conditioning said membrane prior to installing it in said cell.

14. The method of claim 13 wherein said conditioning comprises soaking said membrane at a temperature of between about 80° and about 100° C. in a sodium hydroxide solution containing between about 4M and 6M NaOH for between about 8 and about 10 hours.

15. A method for measuring cationic transport numbers and water transport numbers under a variety of operating conditions for a selected cation exchange permselective membrane in an electrolytic cell having said membrane suspended therein to form an anode compartment and a cathode compartment for containing anolyte and catholyte solutions, respectively, which comprises:
(a) preparing a series of anolyte pairs, each member of said pair having the same anolyte concentration, each anolyte pair having a different anolyte concentration from other pairs in said series, one member of each pair containing a preselected amount of radioactive tracer material;
(b) preparing a series of catholytes, each catholyte having a different preselected catholyte concentration from other members of the series;
(c) conveying a portion of a first anolyte member of a selected anolyte pair to said anode compartment and a portion of a selected first catholyte from said series of catholytes to said cathode compartment, and circulating said first anolyte member and said first catholyte in said cell at a preselected temperature to condition said membrane;
(d) adding additional portions of said first anolyte member and said first catholyte to said cell while subjecting the cell contents to electrolysis at a preselected first current density level for a preselected time period and temperature;
(e) removing and analyzing said first anolyte member and said first catholyte after electrolysis for water concentration and cation concentration;
(f) removing said first anolyte member from said anode chamber and conveying to said anode chamber a portion of a second anolyte member from said pair containing radioactive tracer material while subjecting the cell contents to electrolysis at said preselected first current density level for said preselected time period and temperature;
(g) removing and analyzing said second anolyte member and said first catholyte after electrolysis for water content, cation concentration and radioactive tracer concentration;
(h) repeating steps (c) through (g) at a preselected second current density level; and
(i) repeating steps (c) through (h) until said membrane is tested for each of said pair of anolytes in said series against each catholyte in said series, and calculating water transport numbers and cationic transport numbers for the membrane for each combination of said selected anolytes and said selected catholytes for said first and second preselected current density levels.

16. An automatic electrochemical membrane test cell apparatus for measuring the cationic and water transport properties of a permselective membrane during electrolysis, said apparatus comprising:
(a) a pair of half cells, each containing a horizontally disposed inner chamber, said cell being formed by joining said half cells so that said chambers abut each other to form said cell;
(b) means for sealingly suspending said membrane between said half cells to form separate anode and cathode compartments therein;
(c) electrode means forming an anode in said anode compartment and a cathode in said cathode compartment;
(d) electrolyte fluid storage means comprising a first plurality of individual storage containers for storing anolyte solutions of varying concentration, each of said anolyte solutions being paired with one having an identical concentration but with a preselected amount of radioactive tracer added thereto, and a second plurality of individual storage containers for storing catholyte solutions of varying concentration;
(e) means for sequentially introducing a selected one of said anolyte solutions into said anode compartment and a selected one of said catholyte solutions into said cathode compartment;
(f) heating means for holding said selected, circulating anolyte and catholyte solutions at a preselected temperature level;
(g) means for selecting and implementing a test program wherein the amperage applied to said electrodes for said electrolysis is programably changed from a first discrete value of current density to at least a second discrete value of current density during the course of a test;
(h) means for sequentially controlling the filling and draining of said selected anolyte and catholyte solutions and their flow within the cell; and
(i) means for generating test samples taken from said selected solutions, measuring changes in their concentration resulting from said electrolysis and determining a water and cationic transport data point for each pair of said selected solutions.

17. The apparatus of claim 16 wherein said introduction and circulation means, said heating means, said test program implementation means, said drain and fill means, said test sample generation means and said data point calculation is controlled by centralized automatic control means.

18. The apparatus of claim 17 wherein said heating further comprises sensing and control means to maintain said preset temperature of said electrolyte to ±1° C.

19. The apparatus of claim 16 wherein said half cells are made from an inert material.

20. The apparatus of claim 19 wherein said inert material is polytetrafluoroethylene.

21. The apparatus of claim 16 wherein said heating means comprises a cartridge heater.

22. The apparatus of claim 21 wherein said heater is adapted to heat and hold said anolyte and said catholyte to a temperature in the range from about 60° and about 200° C.

23. The apparatus of claim 21 wherein said heater and said electrode means are combined into a single unit.

24. The apparatus of claim 16 wherein said anode and cathode are foraminous electrodes.

25. The apparatus of claim 7 wherein said anode is a dimensionally stable anode.

26. The apparatus of claim 24 wherein said anode is a titanium screen having a ruthenium oxide/titanium oxide coating thereon.

27. The apparatus of claim 24 wherein said cathode is a platinum screen.

28. The apparatus of claim 24 wherein said cathode is a catalytic cathode.

29. The apparatus of claim 16 wherein said cell electrolysis is conducted at an amperage value of between about 0.5 to about 15 $KA/m^2$.

30. The apparatus of claim 29 wherein said cell electrolysis is conducted at an amperage value of between about 1 to about 10 $KA/m^2$.

31. The apparatus of claim 16 wherein said inner chamber is biconic in shape.

32. The apparatus of claim 16 wherein said membrane is made from a perfluorinated polymer having lateral side chains, said side chains being selected from the group consisting of carboxylic, sulfonic and phosphonic acid functional groups.

33. The apparatus of claim 32 wherein said membrane has carboxylic acid functional side groups.

34. The apparatus of claim 33 wherein said membrane has sulfonic acid functional side groups.

35. The apparatus of claim 16 further comprising sensing means adapted to determine when each of said compartments is filled.

36. The apparatus of claim 16 further comprising preheating means for said anolyte and said catholyte.

37. The apparatus of claim 16 wherein said radioactive tracer is Na-22.

* * * * *

UNITED STATES PATENT AND TRADEMARK OFFICE
CERTIFICATE OF CORRECTION

PATENT NO. : 4,483,748

DATED : November 20, 1984

INVENTOR(S) : Howard L. Yeager, J. David Malinsky

It is certified that error appears in the above-identified patent and that said Letters Patent is hereby corrected as shown below:

In the Abstract, at lines 18 and 19 "considerably" should be --considerable--.

In column 1, at line 12 "volumn" should be --volume--.

In column 9, at line 63 "in" should be --is--.

In column 10, at line 5, after "Nafion® 901" and before "hours" please insert --membrane which had been conditioned for about 12--.

In column 10, at line 57 "inter-relationshps" should be --inter-relationships--.

Signed and Sealed this

Seventh Day of May 1985

[SEAL]

Attest:

DONALD J. QUIGG

*Attesting Officer*   *Acting Commissioner of Patents and Trademarks*